United States Patent
Kozerski et al.

(10) Patent No.: US 12,091,417 B2
(45) Date of Patent: Sep. 17, 2024

(54) 7-ETHYL-10-HYDROXYCAMPTOTHECIN DERIVATIVES FOR USE IN THE TREATMENT OF CANCER

(71) Applicant: Narodowy Instytut Lekow, Warsaw (PL)

(72) Inventors: Lech Kozerski, Warsaw (PL); Beata Naumczuk, Bielsk Podlaski (PL); Jerzy Sitkowski, Warsaw (PL); Elzbieta Bednarek, Warsaw (PL); Magdalena Urbanowicz, Morag (PL); Wojciech Bocian, Warsaw (PL); Katarzyna Wiktorska, Warsaw (PL)

(73) Assignee: NARODOWY INSTYTUT LEKOW, Warsaw (PL)

( * ) Notice: Subject to any disclaimer, the term of this patent is extended or adjusted under 35 U.S.C. 154(b) by 179 days.

(21) Appl. No.: 17/398,016

(22) Filed: Aug. 10, 2021

(65) Prior Publication Data
US 2022/0081448 A1   Mar. 17, 2022

(30) Foreign Application Priority Data
Sep. 17, 2020   (LU) ........................................ 102067

(51) Int. Cl.
*C07D 491/22* (2006.01)

(52) U.S. Cl.
CPC ................................ *C07D 491/22* (2013.01)

(58) Field of Classification Search
CPC ............................. C07D 491/22; A61P 35/00
See application file for complete search history.

(56) References Cited

U.S. PATENT DOCUMENTS

| | | | |
|---|---|---|---|
| 4,473,692 A | 9/1984 | Miyasaka et al. | |
| 4,545,880 A * | 10/1985 | Miyasaka | C07D 491/22 |
| | | | 204/157.72 |
| 5,972,955 A | 10/1999 | Duvvuri et al. | |
| 6,214,836 B1 * | 4/2001 | Duvvuri | A61P 31/00 |
| | | | 514/283 |
| 2010/0010032 A1 | 1/2010 | Fontana et al. | |
| 2015/0266888 A1 | 9/2015 | Kozerski et al. | |

FOREIGN PATENT DOCUMENTS

| | | | | |
|---|---|---|---|---|
| CN | 1704416 A | * | 12/2005 | |
| CN | 103113381 A | | 5/2013 | |
| CN | 105693740 A | | 6/2016 | |
| JP | H03232888 A | | 10/1991 | |
| WO | WO-9746564 A1 | * | 12/1997 | ......... B60R 13/0838 |
| WO | 2011154574 A1 | | 12/2011 | |
| WO | WO-2014064654 A1 | * | 5/2014 | ............. A61P 31/00 |

OTHER PUBLICATIONS

CAS Registry No. 1605283-23-5 [Retrieved from STNext online] [Entered STN: May 15, 2014]. (Year: 2014).*
CAS Registry No. 86639-52-3 [Retrieved from STNext online] [Entered STN: Nov. 16, 1984]. (Year: 1984).*
Lu et al. Method for preparation and application of novel 9-hydrocarbyl-7-ethylcamptothecin derivatives. CN-1704416-A (Dec. 7, 2005). Google patents English machine translation. (Year: 2005).*
Search Report from counterpart Luxembourg Patent Appln. No. LU102067 dated Jun. 11, 2021 (8 pages—pp. 2-8 are in English).
Extended European Search Report issued in corresponding European Patent Application No. 21461575.9 dated Jan. 24, 2022 (7 pages).
Naumczuk et al., "New generation of camptothecin derivatives spontaneously alkylating DNA," New Journal of Chemistry, DOI: 10.1039/c6nj01217e, 2016 (8 pages).
Kingsbury et al., "Synthesis of Water-Soluble (Aminoalkyl) camptothecin Analogues: Inhibition of Topoisomerase I and Antitumor Activity," Journal of Medicinal Chemistry, 1991, vol. 34, pp. 98-107.

* cited by examiner

*Primary Examiner* — Amanda L. Aguirre
(74) *Attorney, Agent, or Firm* — Kilyk & Bowersox, P.L.L.C.

(57) ABSTRACT

The subject of the present invention are water-soluble derivatives of camptothecin, their synthesis and use. These compounds exhibit preferable biological properties for use in anti-neoplasm therapy.

5 Claims, No Drawings

7-ETHYL-10-HYDROXYCAMPTOTHECIN DERIVATIVES FOR USE IN THE TREATMENT OF CANCER

The present invention relates to 7-ethyl-10-hydroxycamptothecin derivatives that are topoisomerase I inhibitors and can be useful in the treatment of cancer.

Topoisomerase I is the enzyme that controls the changes in DNA tridimensional structure by catalyzing the breaking and rejoining (religation) of the phosphodiester backbone of a DNA strand during the normal cell cycle. Inhibition of topoisomerases interferes with transcription and replication by causing DNA damage, inhibition of DNA replication, failure to repair strand breaks, and then cell death.

Naturally occurring compound camptothecin (CPT) and its derivatives are known as very active topoisomerase I inhibitors. They bind to nicked DNA and topoisomerase (I), forming a ternary complex and stabilizing DNA—topoisomerase I interaction, thereby preventing restoration of the double strand. Damage to the replication fork leads to irreversible breakage of the double strand DNA and apoptosis of a cancer cell.

Topoisomerase (I) inhibition is thus an important issue in cancer treatment. 10-Hydroxycamptothecin derivatives, such as topotecan (9-[(dimetyloamino)methyl]-10-hydroxycamptothecin) and irinotecan (7-ethyl-10-[4-(1-piperidino)-1-piperidino]-carbonyloxycamptothecin) are presently used in clinical practice for treating cancer. A serious problem, however, is their high systemic toxicity, often even lethal.

The 7-Ethyl-10-hydroxycamptothecin, also known under the code SN38, is an active metabolite of irinotecan, much more active than irinotecan itself. Clinical use of SN38 is however limited by its very poor aqueous solubility and hydrolysis of the lactone ring at pH>6 to inactive carboxylate form that causes challenges in its effective delivery to cancer cells. Special formulations of SN38 have to be developed to improve its pharmacokinetic properties. Also, high toxicity still remains a serious problem, similarly as in the case of topotecan and irinotecan.

Binding of camptothecin derivatives with nicked DNA in the ternary complexes DNA oligomer/topoisomerase 1/camptothecin that prevents DNA religation is poor.

Recently, certain camptothecin compounds were disclosed that can spontaneously alkylate DNA via stronger covalent binding of a ligand with DNA oligomer.

Water-soluble 7-ethyl-10-hydroxycamptothecin derivatives that are able to spontaneously alkylate DNA via covalent DNA binding are disclosed in WO2014/064654 and Naumczuk, B.; Wiktorska, K.; Lubelska, K.; Kawęcki, R.; Bocian, W.; Bednarek, E.; Sitkowski, J.; Chilmonczyk, Z.; Kozerski, L. New generation of camptothecin derivatives spontaneously alkylating DNA, *New Journal of Chemistry* 2016, 40, 7978-7985. It has been suggested that covalent binding proceeds via a reactive o-methylene quinone intermediate.

Certain alkylamino substituted 7-ethyl-10-hydroxycamptothecin derivatives are disclosed in CN103113381; JPH03232888; WO2008/012003; and WO2011/154574. Water-soluble camptothecin derivatives are also disclosed in Sawada, Seigo et al., "Preparation of anticancer water-soluble camptothecins", CA, Chemical Abstracts Service, Columbus, Ohio, US, (1992), Database accession no. 1992: 83994, and in Kingsbury W. D. et al., "Synthesis of Water-soluble (Aminoalkyl)Camptothecin Analogues: Inhibition of Topoisomerase I and Antitumor Activity", Journal of Medicinal Chemistry, 1991, vol. 34, no. 1, p. 98-107. However, these publications focus on inhibition of topoisomerase I by way of forming ternary complexes DNA oligomer/topoisomerase I/organic ligand.

There is still a large need to provide new anti-cancer camptothecin derivatives with high cytotoxic activity and low toxicity to normal cells, preferably water-soluble camptothecin derivatives.

The present invention relates to novel, water-soluble 7-ethyl-10-hydroxycamptothecin derivatives, exhibiting unexpected advantageous properties which are useful in cancer treatment and are highly effective and less toxic than prior art compounds. The compounds of the invention can form a stable complex with cancer DNA by way of DNA spontaneous alkylation via covalent binding. Such a mechanism ensures high stability of the complex.

The subject of the present invention is compound defined by the formula (I):

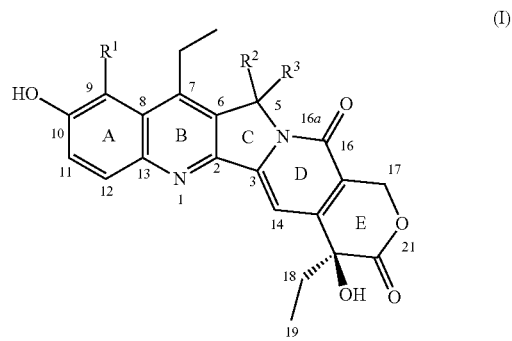

wherein
$R^1$ is selected from the group consisting of hydrogen atom, hydroxymethyl, N—(C3-C4)alkylamino)methyl, N-(2'-hydroxyethyl)methyl, N-(2'-aminoethyl)methyl, N-(2'-glucosamine)methyl, (N-pyrrolidinyl)methyl, and (N-azetidinyl)methyl;

$R^2$ and $R^3$ are independently selected from the group consisting of hydrogen atom, hydroxymethyl, (N-pyrrolidinyl)methyl, and (N-azetidinyl)methyl, with the proviso that one of $R^2$ and $R^3$ can represent hydrogen atom and $R^2$ and $R^3$ represents hydroxymethyl group, except when $R^2$ and $R^3$ together form methylidene group ($=CH_2$).

Compounds of the invention are water-soluble 5-substituted derivatives of 7-ethyl-10-hydroxycamptothecin (also known under the code SN38). Compounds according to the present invention are capable to perform alkylation reaction of the nucleophilic nitrogen atom in bases present in tumor DNA in an effective and easy way. It has been shown that compounds according to the present invention exhibit spontaneous or UV-induced binding with a DNA oligomer. Preferably, compounds of formula (I) are selected from the group comprising:

5-(R)—(N-pyrrolidinyl)methyl-7-ethyl-10-hydroxycamptothecin, 5-(S)—(N-pyrrolidinyl)methyl-7-ethyl-10-hydroxycamptothecin, 5-(R)-hydroxymethyl-7-ethyl-10-hydroxycamptothecin, 5-(S)-hydroxymethyl-7-ethyl-10-hydroxycamptothecin, 5-(S)—(N-azetidinyl)methyl-7-ethyl-9-hydroxymethyl-10-hydroxycamptothecin, 5-(R)—(N-azetidinyl)methyl-7-ethyl-9-hydroxymethyl-10-hydroxycamptothecin, 5-(S)—(N-azetidinyl)methyl-7-ethyl-9-(N-azetidinyl)
methyl-10-hydroxycamptothecin,
5-(R)—(N-azetidinyl)methyl-7-ethyl-9-(N-azetidinyl)
methyl-10-hydroxycamptothecin,
5-(R)-hydroxymethyl-7-ethyl-9-(N-azetidinyl)methyl-10-hydroxycamptothecin,
5-(S)-hydroxymethyl-7-ethyl-9-(N-azetidinyl)methyl-10-hydroxycamptothecin,
5-(S)-hydroxymethyl-7-ethyl-9-hydroxymethyl-10-hydroxycamptothecin,
5-(R)-hydroxymethyl-7-ethyl-9-hydroxymethyl-10-hydroxycamptothecin,
5-methylidene-7-ethyl-10-hydroxycamptothecin, and
5,5-bis(hydroxymethyl)-7-ethyl-10-hydroxycamptothecin.

In a further embodiment of compounds of formula (I), $R^1$ represents hydrogen atom, $R^2$ and $R^3$ are selected from the group comprising: hydrogen atom, hydroxymethyl and (N-pyrrolidinyl)methyl with the proviso that only one of $R^2$ and $R^3$ can represent hydrogen atom $R^2$ and/or $R^3$ represents hydroxymethyl group. Preferred compounds are selected from the group comprising:
5-(R)—(N-pyrrolidinyl)methyl-7-ethyl-10-hydroxycamptothecin,
5-(S)—(N-pyrrolidinyl)methyl-7-ethyl-10-hydroxycamptothecin,
5-(R)-hydroxymethyl-7-ethyl-10-hydroxycamptothecin, and
5-(S)-hydroxymethyl-7-ethyl-10-hydroxycamptothecin.

In a further embodiment of compounds of formula (I), $R^1$ represents (N-azetidinyl)methyl, $R^2$ and $R^3$ are selected from the group comprising: hydrogen atom, hydroxymethyl with the proviso that only one of $R^2$ and $R^3$ can represent hydrogen atom. Preferred compounds are selected from the group comprising:
5-(S)-hydroxymethyl-7-ethyl-9-(N-azetidinyl)methyl-10-hydroxycamptothecin, and
5-(R)-hydroxymethyl-7-ethyl-9-(N-azetidinyl)methyl-10-hydroxycamptothecin.

The compounds of the invention as defined above are able to kill cancer cells, as shown below, and can be used as a medicament.

In a further aspect, the object of the present invention is therefore the compound of formula (I) as defined above, for use as medicament.

In a yet further aspect, the object of the present invention is therefore a pharmaceutical composition comprising the compound of formula (I) as defined above, together with pharmaceutically acceptable excipient(s).

In a yet further aspect, the object of the present invention is therefore the compound of formula (I), as defined above, for use in a method of treatment of cancer, in particular in a human subject in need of such treatment.

The method of treatment of cancer comprises administering the compound of formula (I), as defined above, to a human subject in need of such treatment.

The said cancer includes in particular solid tumors, such as breast cancer, colon cancer, lung cancer, and brain glioma.

The said cancer includes also hematological cancer, in particular leukemia.

Compounds of formula (I) wherein as defined above can be obtained by reaction of 7-ethyl-10-hydroxycamptothecin with an appropriate amine, preferably pyrrolidine or azetidine, in an environment of acetonitrile with acetic acid or without acetic acid at reflux temperature wherein a mixture of compounds of the formula (I). Said mixture can be resolved utilizing preparative chromatography. The manner of resolution is described below in the Examples.

In a further embodiment compounds of the invention of formula (I), substituted at the position 9 with N-(alkylamino)methyl substituents, may undergo a transformation into the intermediate o-methylenequinone compound QM

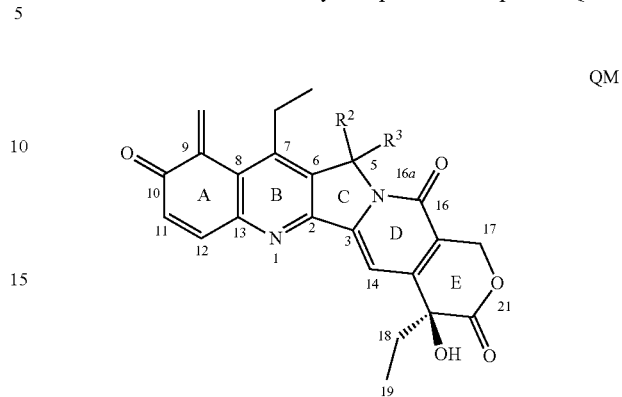

wherein $R^2$ represents H and $R^3$ represents (N-azetidinyl) methyl, or (N-pyrrolidinyl)methyl, or hydroxymethyl.
or $R^2$ represents (N-azetidinyl)methyl, or (N-pyrrolidinyl)methyl, or hydroxymethyl and $R^3$ represents H Compound QM may react in situ with the nucleophilic centres in duplex DNA, as outlined in Scheme 1, whereas compounds according to the present invention, described by formula (I), can also act as DNA intercalators.

Scheme 1

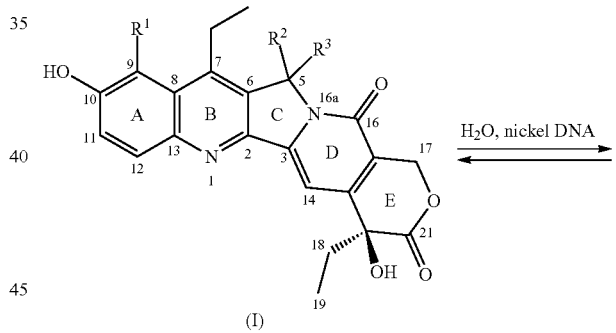

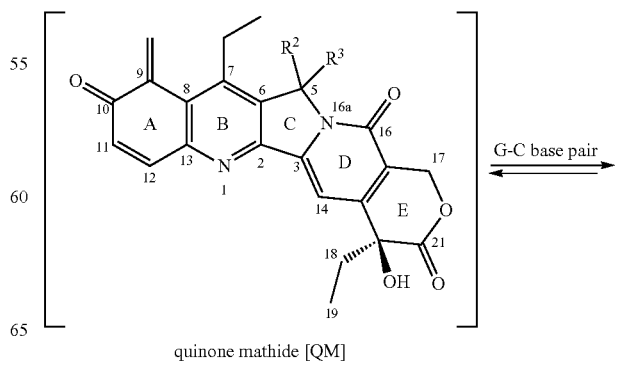

quinone mathide [QM]

-continued

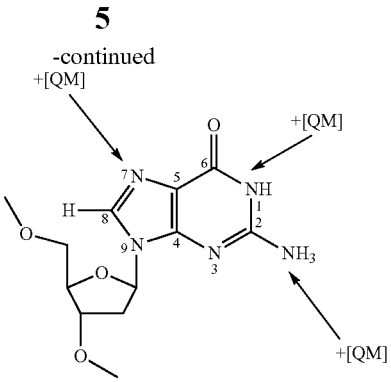

Selected compounds of the present invention were tested in biological systems using various cancer cell lines, including blood cancer lines, and showed high $IC_{50}$ parameter values.

In a light of the above, the present invention may constitute a breakthrough in chemotherapy due to the surprisingly advantageous properties of the claimed compounds, thus delivering an effective tool for combating neoplastic diseases. Even more important is a fact that all tested compounds of the invention are at least an order of magnitude less toxic than SN38 (7-ethyl-10-hydroxycamptothecin), and in preferred cases are practically nontoxic against normal cells ($IC_{50}$>1000).

The present invention is described in more details in the following Examples, wherein HPLC, ESI MS, ECD and NMR experiments were performed as described below.

HPLC Experimental Details

Chromatography in a reversed phase system, C-18, was performed using a semi-preparative column Phenomenex Gemini 5 μm NX-C18 110 Å 250×10 mm on HPLC Shimadzu LC-20AT with autosampler SIL 10AF, fraction collector FRC-10A and detector SPD-M20A.

ESI MS Experimental Details

The Hight Resolution ESI MS spectra were performed on Ultra-Performance Liquid Chromatograph ACQUITY UPLC I-Class (Waters Inc.) coupled with Synapt G2-S HDMS (Waters Inc.) mass spectrometer equipped with an electrospray ion source and q-TOF type mass analyzer. The instrument was controlled and recorded data were processed using MassLynx V4.1 software package (Waters Inc.).

NMR Experiments $^1$H NMR spectra were obtained using a VARIAN VNMRS 500 MHz spectrometer using a Nalorac ID probe equipped with a gradient unit generating a gradient of 60 Gs/cm along the —Z-axis, at a temperature of 25.0° C. Chemical shifts were referenced vs TSPA as an internal standard dissolved in $D_2O$.

The parameters of the $^1$H NMR analysis were: 25.3° C.; sw=8000 Hz (spectrum range); nt=16, or 64, or 256; (number of scans), 32 K memory points; at=2 s (acquisition time), d1=6 s (relaxation delay), satdly=2 s (presaturation delay), lb=0.3 Hz (line broadening).

Parameters of the $^{13}$C NMR analysis; 25.0° C.

The $^1$H/$^{13}$C-HSQC. $^1$H-$^{13}$C HSQC spectra (heteronuclear single quantum correlation) were obtained using a spectrum range of 5000 Hz, 2048 points in the $^1$H domain and 8000 Hz, 800×2 increments in the $^{13}$C domain; 128 scans per increment $t_1$, with a relaxation delay of 1 s and $^1$J(C, H)=135 Hz. The data were linearly extrapolated to 1600 points and filled with zeros to 4096 points in $F_1$ before a Fourier transformation.

$^1$H/$^{13}$C-HMBC spectra (heteronuclear multiple bonds correlation) HMBC spectra with a gradient coherence of $^1$H-$^{13}$C were obtained, using an acquisition time of 0.2 s, $^1$H–90° impulse width of 7.8 μs, $^{13}$C—90° pulse width of 11.5 μs, spectrum range of 5000 Hz, 2048 given points in the $^1$H dimension and 25000 Hz, 1024 increments in the $^{13}$C dimension, and a relaxation delay of 1.2 s. Data were obtained in the form of absolute values, using 64 scans per $t_1$ increment. The experiment was optimized for $^n$J(C,H)=8 Hz, and for $^1$J(C,H)=140 Hz with a low-pass filter. The data were linearly extrapolated to 2048 points and filled with zeros to 4096 points in $F_1$ before the Fourier transformation.

CD Measurements

The experimental ECD spectra were recorded using a Jasco (Tokyo, Japan) J-715 and Jasco J-815 spectrometers at room temperature in spectroscopic grade $CH_3OH$ and $CD_3CN$ in a quartz cell with a path length of 0.5 cm. All spectra were measured using a scanning speed of 100 nm min−1, a step size of 0.5 nm, a bandwidth of 1 nm, a response time of 0.5 s, and an accumulation of five scans. The spectra were background corrected using spectra of respective solvents recorded under the same conditions. UV-Vis spectra were measured on a Varian (Palo Alto, CA) spectrophotometer Carry 100E or a Jasco V-670 UV-Vis spectrophotometer just before the ECD measurements.

EXAMPLE I

Preparation of:
5-(R)—(N-pyrrolidinyl)methyl-7-ethyl-10-hydroxycamptothecin 1
5-(S)—(N-pyrrolidinyl)methyl-7-ethyl-10-hydroxycamptothecin 2
5-(R)-hydroxymethyl-7-ethyl-10-hydroxycamptothecin 3
5-(S)-hydroxymethyl-7-ethyl-10-hydroxycamptothecin 4
5-methylidene-7-ethyl-10-hydroxycamptothecin 5

Experimental Procedure

SN38 (7-ethyl-10-hydroxycamptothecin×$H_2O$) (5.26 mg; 0.0128 mmol) was suspended in 7.5 mL $CH_3CN$, and then 37% aqueous $CH_2O$ (12.5 μL; 0.154 mmol), and 12.5 μL pyrrolidin (0.154 mmol) were added. The resulting mixture was stirred at 80° C. After 6 h the solvent was evaporated off under vacuum and residue was rinsed with diethyl ether (3×1 mL). The residue was purified using HPLC on Phenomenex Gemini 5 μm NX-C18 110 Å, 250×10 mm column using the liquid phase system: $CH_3CN$/aqueous 0.1% HCOOH at a flow rate of 3 mL/min. using the following gradient: 15% $CH_3CN$ through 10 min., 20% to 13 min. and 50% from 22 min. The course of the chromatography was monitored using UV detection at a wavelength of 260 nm.

Fractions were collected with retention time 11.8 min, (1) 13.6 min (2), 20.7 min (3), 22.1 (4) and 27.8 min (5) and were lyophilized. Products were converted to the hydrochloride salt using 0.5% aqueous HCl (3 mL) and lyophilized yielding pure products (yield >98%).

Spectral data of: 5-(R)—(N-pyrrolidinyl)methyl-7-ethyl-10-hydroxycamptothecin 1 retention time 11.8 min (Yield 7%)

HR-MS (ESI): calculated for $C_{27}H_{30}N_3O_5$[M+H]$^+$: 476.2185, measured: 476.2185.

$^1$H NMR δ ($D_2O$, pH=3.5, TSPA) 500 MHz: 0.97 (t, J=7.7 Hz, 3H), 1.51 (t, J=7.3 Hz, 3H), 2.00 (bs, 1H) 2.00 (m, 2H), 2.13 (bs, 2H), 2.26 (bs, 1H), 3.03 (bs, 1H), 3.18 (m, 1H), 3.27 (m, 1H), 3.35 (bs, 1H), 3.51 (bs, 1H), 3.72 (dd, J=15.0 Hz, J=7.4 Hz, 1H), 3.99 (d, J=15.0 Hz, 1H), 4.21 (bs, 1H), 5.44 (1/2 AB, J=16.5 Hz, 1H), 5.53 (1/2 AB, J=16.5 Hz, 1H), 6.19 (d, J=7.4 Hz, 1H, (C5-H)), 7.36 (s, 1H), 7.34 (dd, J=8.8 Hz, J=2.2 Hz, 1H), 7.49 (d, J=2.2 Hz, 1H), 7.57 (d, J=8.8 Hz, 1H).

$^{13}$C NMR δ (D$_2$O, TSPA); HSQC, HMBC: 7.0, 13.7, 22.4, 22.5, 23.0, 30.6, 54.8, 56.0, 57.2, 60.5 (C5), 65.8, 73.6, 99.1, 106.3, 119.5, 123.5, 125.6, 130.4, 143.8, 145.4, 146.6, 151.8, 174.9.

UV (D$_2$O, d=0.5 cm) 223 nm, 268 nm, 381 nm.

IR (film in CD$_3$CN): 658, 1637, 3451 cm$^{-1}$.

Spectral data of: 5-(S)(N-pyrrolidinyl)methyl-7-ethyl-10-hydroxycamptothecin 2 retention time 13.6 min (Yield 8%)

HR-MS (ESI): calculated for C$_{27}$H$_{30}$N$_3$O$_5$[M+H]$^+$: 476.2185, measured: 476.2185.

$^1$H NMR δ (D$_2$O, pH=3.5, TSPA) 500 MHz: 0.97 (t, J=7.3 Hz, 3H), 1.40 (t, J=7.7 Hz, 3H), 2.01 (bs, 1H) 2.01 (m, 2H), 2.12 (bs, 2H), 2.24 (bs, 1H), 3.13 (bs, 1H), 3.20 (m, 2H), 3.36 (bs, 1H), 3.63 (bs, 1H), 3.51 (bs, 1H), 3.96 (dd, J=15.0 Hz, J=7.3 Hz, 1H), 4.13 (d, J=15.0 Hz, 1H), 4.06 (bs, 1H), 5.43 (1/2 AB, J=16.1 Hz, 1H), 5.66 (1/2 AB, J=16.1 Hz, 1H), 6.32 (d, J=7.3 Hz, 1H, (C5-H)), 7.47 (dd, J=8.8 Hz, J=2.5 Hz, 1H), 7.55 (s, 1H), 7.49 (1H), 7.96 (d, J=8.8 Hz, 1H).

$^{13}$C NMR δ (D$_2$O, TSPA); HSQC, HMBC: 7.1, 13.6, 22.4, 23.0, 30.6, 54.8, 56.3, 57.1, 60.4 (C5), 65.9, 73.7, 99.7, 106.5, 119.6, 123.4, 126.3, 129.1, 130.6, 144.0, 145.7, 146.5, 147.7, 152.0, 156.0.

UV (D$_2$O, d=0.5 cm) 268 nm, 331 nm, 368 nm, 381 nm.

IR (film in CD$_3$CN): 616, 1637, 3394 cm$^{-1}$.

Spectral data of: 5-(R)hydroxymethyl-7-ethyl-10-hydroxycamptothecin 3 retention time: 20.7 min (Yield 7%)

HR-MS (ESI): calculated for C$_{23}$H$_{23}$N$_2$O$_6$ [M+H]$^+$: 423.1556, measured: 423.1545.

$^1$H NMR δ (D$_2$O, pH=3.0, TSPA) 500 MHz: 0.93 (t, J=7.4 Hz, 3H), 1.28 (t, J=7.7 Hz, 3H), 1.93 (q, J=7.4 Hz, 2H), 2.99 (m, 1H), 3.15 (m, 1H), 4.07 (dd, J=12.8 Hz, J=2.2 Hz, 1H), 4.64 (dd, J=12.8 Hz, J=2.2 Hz, 1H), 5.36 (1/2 AB, J=16.1 Hz, 1H), 5.51 (1/2 AB, J=16.1 Hz, 1H), 5.51 (1H, C5-H)), 7.20 (d, J=2.6 Hz, 1H), 7.29 (s, 1H), 7.29 (dd, J=9.2 Hz, J=2.6 Hz, 1H), 7.76 (d, J=9.2 Hz, 1H).

$^{13}$C NMR δ (D$_2$O, TSPA); HSQC, HMBC: 6.8, 13.1, 22.0, 30.5, 57.7, 64.6, (C5) 65.9, 73.3, 97.7, 105.7, 118.9, 122.7, 127.3, 128.3, 129.8, 142.6, 145.2, 150.6, 155.3, 174.7.

UV (DMSO, d=0.5 cm) 270 nm, 338 nm, 372 nm, 390 nm.

IR (film in CD$_3$CN): 1034, 1056, 1110, 1165, 1229, 1290, 1379, 1468, 1515, 1560, 1589, 1619, 1651, 1741, 2977, 3419 cm$^{-1}$.

Spectral data of: 5-(S)-hydroxymethyl-7-ethyl-10-hydroxycamptothecin 4 retention time: 22.1 min (Yield 10%)

HR-MS (ESI): calculated for C$_{23}$H$_{23}$N$_2$O$_6$ [M+H]+: 423.1556, measured: 423.1545.

$^1$H NMR δ (CD$_3$CN) 500 MHz: 0.95 (t, J=7.4 Hz, 3H), 1.38 (t, J=7.8 Hz, 3H), 1.90 (m, 2H), 3.23 (m, 2H), 4.06 (dd, J=12.2 Hz, J=2.4 Hz, 1H), 4.69 (dd, J=12.2 Hz, J=2.4 Hz, 1H), 5.29 (1/2 AB, J=16.1 Hz, 1H), 5.55 (1/2 AB, J=16.1 Hz, 1H), 5.92 (t, J=2.4 Hz, 1H, C5-H)), 7.52 (d, J=2.9 Hz, 1H), 7.52 (s, 1H), 7.49 (dd, J=9.3 Hz, J=2.9 Hz, 1H), 8.26 (d, J=9.3 Hz, 1H).

$^{13}$C NMR δ (CD$_3$CN); HSQC, HMBC: 7.0, 13.3, 22.2, 30.9, 59.3, 65.4, (C5) 65.8, 72.8, 105.9, 120.0, 123.1, 129.3, 129.5, 129.7, 146.4, 149.9, 156.4, 157.9, 173.1.

UV (DMSO, d=0.5 cm) 270 nm, 338 nm, 372 nm, 390 nm.

IR (film in CD$_3$CN): 1065, 1461, 1511, 1593, 1623, 1741, 3420 cm$^{-1}$.

Example II

Preparation of:
5-(R)-hydroxymethyl-7-ethyl-9-(N-azetidinyl)methyl-10-hydroxycamptothecin 6
5-(S)-hydroxymethyl-7-ethyl-9-(N-azetidinyl)methyl-10-hydroxycamptothecin 7
5,5-bis(hydroxymethyl)-7-ethyl-10-hydroxycamptothecin 8
5-(R)-hydroxymethyl-7-ethyl-10-hydroxycamptothecin 3
5-(S)-hydroxymethyl-7-ethyl-10-hydroxycamptothecin 4
5-methylidene-7-ethyl-10-hydroxycamptothecin 5
Experimental Procedure SN38 (7-ethyl-10-hydroxycamptothecin×H$_2$O) (4.46 mg; 10.9×10$^{-3}$ mmol) was suspended in 3 ml CH$_3$CN and then 37% aqueous CH$_2$O (10.6 μL; 0.13 mmol) and 7.6 μl 98% azetidine (0.13 mmol) were added. The resulting mixture was stirred at 80° C. The reaction was ended after 30 min after the moment when the substrate was dissolved. The solvent was evaporated off under vacuum and residue was rinsed with diethyl ether (3×1 mL). The residue was purified using HPLC on an Phenomenex Gemini 5 μm NX-C18 110 Å, 250×10 mm column using the liquid phase system: CH$_3$CN/aqueous 0.1% HCOOH at a flow rate of 3 mL/min. using the following gradient: 15% CH$_3$CN through 7 min., 20% to 13 min. and 50% from 20 min. The course of the chromatography was monitored using UV detection at a wavelength of 260 nm. Fractions were collected with retention times: 5.7 min. (6), 11.0 min. (7), 20.7 min. (8) 22.0 min. (3), 22.8 min. (4), 27.1 min (5) and were lyophilized. Products were converted to the hydrochloride salt using 0.5% aqueous HCl (3 ml) and lyophilized yielding pure products (>96%).

The synthesised diastereomeric compounds of the same mass are numbered in latin numbers beginning with lower retention time in HPLC separation.

Spectral data of: 5-(R)-hydroxymethyl-7-ethyl-9-(N-azetidinyl)methyl-10-hydroxycamptothecin 6 retention time: 5.7 min Yield 14%.

HR-MS (ESI): calculated for C$_{27}$H$_{30}$N$_3$O$_6$[M+H]$^+$: 492.2135, measured: 492.2132.

$^1$H NMR δ (D$_2$O, pH=3.5, TSPA) 500 MHz: 0.98 (t, J=7.3 Hz, 3H), 1.31 (t, J=7.3 Hz, 3H), 2.02 (q, J=7.3 Hz, 2H), 2.41 (m, 1H), 2.49 (m, 1H), 3.35 (m, 2H), 4.08 (m, 2H), 4.18 (m, 1H), 4.24 (m, 1H), 4.32 (dd, J=13.2 Hz, J=2.2 Hz, 1H), 4.75 (overlapped in D$_2$O, 1H), 5.03 (1/2 AB, J=14.7 Hz, 1H), 5.13 (1/2 AB, J=14.7 Hz, 1H), 5.45 (1/2 AB, J=16.4 Hz, 1H), 5.60 (1/2 AB, J=16.4 Hz, 1H), 6.06 (bs, 1H, C5-H), 7.48 (s, 1H), 7.56 (d, J=9.5 Hz, 1H), 8.04 (d, J=9.5 Hz, 1H).

$^{13}$C NMR δ (D$_2$O, TSPA); HSQC, HMBC: 7.1, 16.1, 13.8, 25.7, 30.7, 50.7, 54.7, 58.6, 66.2, 65.5, (C5) 74.0, 98.2, 109.9, 121.9, 127.8, 131.6, 133.5, 145.2, 145.3, 146.4, 149.0, 151.0, 157.2, 175.1.

UV (D$_2$O, d=0.5 cm) 226 nm, 270 nm, 335 nm, 381 nm.

IR (film in CD$_3$CN): 665, 1057, 1166, 1245, 1291, 1398, 1468, 1515, 1645, 1735, 3441 cm$^{-1}$.

Spectral data of: 5-(S)-hydroxymethyl-7-ethyl-9-(N-azetidinyl)methyl-10-hydroxycamptothecin 7 retention time: 11.0 min (Yield 16%)

HR-MS (ESI): calculated for C$_{27}$H$_{30}$N$_3$O$_6$[M+H]$^+$: 492.2135, measured: 492.2132.

$^1$H NMR δ (D$_2$O, pH=4, TSPA) 500 MHz: 0.97 (t, J=7.6 Hz, 3H), 1.27 (t, J=7.6 Hz, 3H), 2.01 (q, J=7.6 Hz, 2H), 2.41 (m, 1H), 2.50 (m, 1H), 3.35 (m, 2H), 4.07 (m, 2H), 4.21 (m, 2H), 4.32 (dd, J=12.5 Hz, J=1.5 Hz, 1H), 4.77 (overlapped in D$_2$O, 1H), 5.05 (1/2 AB, J=14.3 Hz, 1H), 5.12 (1/2 AB, J=14.3 Hz, 1H), 5.43 (1/2 AB, J=16.1 Hz, 1H), 5.64 (1/2 AB, J=16.1 Hz, 1H), 6.17 (bs, 1H, C5-H), 7.55 (s, 1H), 7.65 (d, J=9.4 Hz, 1H), 8.16 (d, J=9.4 Hz, 1H).

$^{13}$C NMR δ (D$_2$O, TSPA); HSQC, HMBC: 9.6, 16.1, 18.5, 28.0, 32.9, 53.2, 57.1, 60.8, 67.9, (C5) 68.6, 76.1, 101.0, 111.6, 122.1, 124.4, 130.2, 134.1, 136.1, 147.6, 147.9, 149.0, 151.8, 153.5, 159.6, 161.0, 177.6.

UV ($D_2O$, d=0.5 cm) 226 nm, 270 nm, 334 nm, 380 nm.

IR (film in $CD_3CN$):628, 1040, 1245, 1467, 1515, 1641, 2256, 3435 cm$^{-1}$.

Spectral data of: 5,5-bis(hydroxymethyl)-7-ethyl-10-hydroxycamptothecin 8 retention time: 20.7 min (Yield 10%)

HR-MS (ESI): calculated for $C_{24}H_{25}N_2O_2[M+H]^+$: 453.1662, measured: 453.1651.

$^1$H NMR δ ($D_2O$, pH=6, TSPA) 500 MHz: 1.00 (t, J=7.4 Hz, 3H), 1.40 (t, J=7.4 Hz, 3H) 2.03 (m, 2H), 3.34 (q, J=7.4 Hz, 2H), 4.41 (dd, J=12.5 Hz, J=6.2 Hz, 2H), 5.08 (dd, J=12.0 Hz, J=6.2 Hz, 2H), 5.44 (1/2 AB, J=16.1 Hz, 1H), 5.61 (1/2 AB, J=16.1 Hz, 1H), 7.56 (s, 1H), 7.55 (dd, J=8.8 Hz, J=2.9 Hz, 1H), 7.60 (d, J=2.9 Hz, 1H), 8.08 (d, J=8.8 Hz, 1H).

$^{13}$C NMR δ ($D_2O$, TSPA); HSQC, HMBC: 6.9, 13.4, 20.6, 30.4, 58.2, 66.1, 73.3, 81.6, 97.6, 106.4, 120.1, 122.9, 128.4, 129.4, 130.4, 143.7, 145.8, 146.0, 147.0, 150.4, 155.4, 175.0.

UV (DMSO, d=0.5 cm) 252, 271 nm, 340 nm, 374 nm, 392 nm.

IR (film in $CD_3CN$): 1005, 1044, 1074, 1101, 1121, 1166, 1232, 1382, 1401, 1460, 1514, 1592, 1658, 1736, 2979, 3378 cm$^{-1}$.

Spectral data of: 5-(R)-hydroxymethyl-7-ethyl-10-hydroxycamptothecin 3 retention time: 22.0 min. (Yield 17%)

HR-MS (ESI): calculated for $C_{23}H_{23}N_2O_6$ [M+H]$^+$: 423.1556, measured: 423.1545.

$^1$H NMR δ ($D_2O$, pH=3.0, TSPA) 500 MHz: 0.93 (t, J=7.4 Hz, 3H), 1.28 (t, J=7.7 Hz, 3H), 1.93 (q, J=7.4 Hz, 2H), 2.99 (m, 1H), 3.15 (m, 1H), 4.07 (dd, J=12.8 Hz, J=2.2 Hz, 1H), 4.64 (dd, J=12.8 Hz, J=2.2 Hz, 1H), 5.36 (1/2 AB, J=16.1 Hz, 1H), 5.51 (1/2 AB, J=16.1 Hz, 1H), 5.51 (1H, C5-H), 7.20 (d, J=2.6 Hz, 1H), 7.29 (s, 1H), 7.29 (dd, J=9.2 Hz, J=2.6 Hz, 1H), 7.76 (d, J=9.2 Hz, 1H).

$^{13}$C NMR δ ($D_2O$, TSPA); HSQC, HMBC: 6.8, 13.1, 22.0, 30.5, 57.7, 64.6, (C5) 65.9, 73.3, 97.7, 105.7, 118.9, 122.7, 127.3, 128.3, 129.8, 142.6, 145.2, 150.6, 155.3, 174.7.

UV (DMSO, d=0.5 cm) 270 nm, 338 nm, 372 nm, 390 nm.

IR (film in $CD_3CN$): 1034, 1056, 1110, 1165, 1229, 1290, 1379, 1468, 1515, 1560, 1589, 1619, 1651, 1741, 2977, 3419 cm$^{-1}$.

Spectral data of 5-(S)-hydroxymethyl-7-ethyl-10-hydroxycamptothecin 4 retention time: 22.8.0 min (Yield 20%)

HR-MS (ESI): calculated for $C_{23}H_{23}N_2O_6$ [M+H]$^+$: 423.1556, measured: 423.1545.

$^1$H NMR δ ($CD_3CN$) 500 MHz: 0.95 (t, J=7.4 Hz, 3H), 1.38 (t, J=7.8 Hz, 3H), 1.90 (m, 2H), 3.23 (m, 2H), 4.06 (dd, J=12.2 Hz, J=2.4 Hz, 1H), 4.69 (dd, J=12.2 Hz, J=2.4 Hz, 1H), 5.29 (1/2 AB, J=16.1 Hz, 1H), 5.55 (1/2 AB, J=16.1 Hz, 1H), 5.92 (t, J=2.4 Hz, 1H, C5-H)), 7.52 (d, J=2.9 Hz, 1H), 7.52 (s, 1H), 7.49 (dd, J=9.3 Hz, J=2.9 Hz, 1H), 8.26 (d, J=9.3 Hz, 1H).

$^{13}$C NMR δ ($CD_3CN$); HSQC, HMBC: 7.0, 13.3, 22.2, 30.9, 59.3, 65.4, (C5) 65.8, 72.8, 105.9, 120.0, 123.1, 129.3, 129.5, 129.7, 146.4, 149.9, 156.4, 157.9, 173.1.

UV (DMSO, d=0.5 cm) 270 nm, 338 nm, 372 nm, 390 nm.

IR (film in $CD_3CN$): 1065, 1461, 1511, 1593, 1623, 1741, 3420 cm$^{-1}$.

Spectral data of: 5-methylidene-7-ethyl-10-hydroxycamptothecin 5 retention time: 27.1 min (Yield 8%)

HR-MS (ESI): calculated for $C_{23}H_{21}N_2O_5$ [M+H]$^+$: 405.1450, measured: 405.1451.

$^1$H NMR δ (DMSO) 500 MHz: 0.87 (t, J=7.5 Hz, 3H), 1.33 (t, J=7.8 Hz, 3H), 1.85 (m, 2H), 3.33 (q, J=7.8, 2H), 5.42 (1/2 AB, J=16.5 Hz, 1H), 5.47 (1/2 AB, J=16.5 Hz, 1H), 6.21 (d, J−1.33 Hz, 1H), 7.33 (s, 1H), 7.45, 7.47 (dd, J=9.3 Hz, J=2.4 Hz, 1H), 7.52 (d, J=2.4 Hz, 1H), 7.62 (d, J=1.6 Hz, 1H), 8.03 (d, J=9.3 Hz, 1H).

$^{13}$C NMR δ (DMSO); HSQC, HMBC: 8.33, 13.0, 21.0, 30.9, 66.0, 72.7, 96.7, 105.8, 108.0, 121.2, 121.3, 123.9, 129.3, 132.1, 141.2, 142.4, 144.1, 146.9, 144.9, 148.8, 157.5, 158.5, 172.7

UV ($H_2O/CH_3CN$), d=0.5 cm) 200 nm, 314 nm, 369 nm, 390 nm, 405 nm.

IR (film in $CD_3CN$): 1065, 1461, 1511, 1593, 1623, 1741, 3420 cm$^{-1}$

Example III

Biological Assays In Vitro $IC_{50}$ Determination Using the Photometric Assay.

All cell lines, MCF7, HT29, HL60, A549 and CRL1790 were purchased from ATCC (American Cell Culture Collection). As exemplified the MCF-7 human breast cancer, the cell line was grown in Iscove's Modified Dulbecco's Medium, supplemented with 10% heat-inactivated fetal bovine serum, penicillin (100 Ul/mL), streptomycin (100 μg/mL), amphotericin (250 ng/mL), L-glutamine (2 mM) and 1% non-essential amino acids solution. The culture of HL-60 human leukemia cells was conducted in Iscove's Modified Dulbecco's Medium, supplemented with 20% heat-inactivated fetal bovine serum, penicillin (100 Ul/mL), streptomycin (100 μg/mL), amphotericin (250 ng/mL), L-glutamine (2 mM) and 1% non-essential amino acids solution.

The cells were grown at 37° C. in a humidified atmosphere containing 5% $CO_2$. After 80% confluence was reached, the adherent MCF7, HL-60, cells were detached with a 0.25% trypsin solution and seeded in 96-well plates at a density of 5×104 cells/mL, 5×105 cells/mL, respectively.

After overnight incubation, the increasing concentrations (0.1-20 μM) of studied compounds dissolved in DMSO were added to the wells. Pure DMSO diluted at the ratio of 1:1000 (v/v) in growth media was added to control wells. After 24, 48 or 72 hours of incubation the MTT-cell proliferation test was performed.

The test exploits the ability of living cells mitochondrial dehydrogenases to convert water-soluble 3-(4,5-dimethyl-thiazol-2-yl)-2,5-diphenyltetrazolium bromide (MTT) to non-soluble formazan. Briefly, after 3 hours incubation of cells with MTT solution the absorbance of formazan dissolved in isopropyl alcohol was measured in a Power Wavex microplate spectrophotometer (BioTek Instruments) at 570 nm.

In order to compare the cytotoxicity of studied compounds the $IC_{50}$ values (the concentrations which induce the cell viability decreased to 50% of the control) were determined. The normalized MTT data were fitted to log(inhibitor) vs. response-variable slope model ($R^2$>0.9) described by the Equation 1 using Prism 5 ver 5.03 (GraphPad Software, Inc):

$$V = \frac{100}{1 + 10^{(logIC50-c) \cdot h}} \quad (1)$$

where: V—cell viability, c—compound concentration, h—Hill coefficient.

As a result log $IC_{50}$ with the standard error were calculated. The goodness of fit ($R^2$) was always above 0.9 and log $IC_{50}$ standard error value did not exceed 10% of the parameter's value.

As comparative compounds, compounds 2a (CC1) and 2b (CC2) disclosed in Naumczuk, B.; Wiktorska, K.; Lubelska, K.; Kawęcki, R.; Bocian, W.; Bednarek, E.; Sitkowski, J.; Chilmonczyk, Z.; Kozerski, L. New generation of camptothecin derivatives spontaneously alkylating DNA, *New Journal of Chemistry* 2016, 40, 7978-7985, were tested. The results of the tests are presented in Table 1.

The results of the tests show that the compounds of a present invention have comparable cytotoxic activity to SN38, however they are few or several orders of magnitude less toxic to normal cells. The latter property is even more appreciated than cytotoxicity as pharmacotherapeutic properties for humans are concerned. Moreover, in a preferable cases compounds of the present invention are nontoxic having $IC_{50}$>1000 for normal cells. It is also worth noting that in a case of pyrrolidine substituent in a present invention its substitution in 5-(S) configuration results in twice reduced $IC_{50}$ (0.007) as compared to the CC1 (N-azetidinyl)methyl-7-ethyl-10-hydroxycamptothecin
CC2 (N-pyrrolidinyl)methyl-7-ethyl-10-hydroxycamptothecin
compound CC2 (IC50 0.014) of the prior art in which the substituent is placed in position C-9. The present invention describes very precise experimental procedure for separation of diastereomers and therefore one can choose more active one and thus avoid administration to the patient an unnecessary burden of a less active compound. The facts above can be considered as a proof of essential novelty of a present invention over the prior art.

The invention claimed is:
1. A compound according to formula (I)

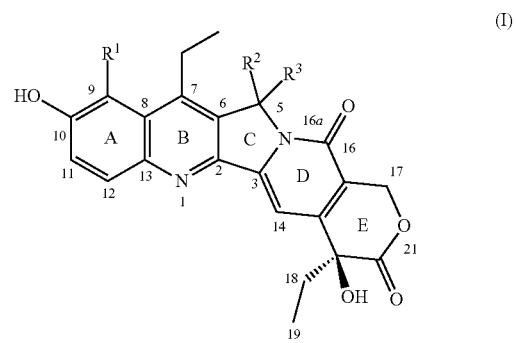

(I)

wherein
$R^1$ is selected from the group consisting of hydrogen atom, hydroxymethyl, N-(C3-C4)alkylamino)methyl, N-(2'-hydroxyethyl)aminomethyl, N-(2'-aminoethyl) aminomethyl, N-(2'-(glucosamine)aminomethyl, (N-pyrrolidinyl)methyl, and (N-azetidinyl)methyl;
$R^2$ and $R^3$ are independently selected from the group consisting of hydrogen atom, hydroxymethyl, (N-pyrrolidinyl)methyl, and (N-azetidinyl)methyl or together form a methylidene group (=$CH_2$), with the proviso that only one of $R^2$ and $R^3$ represents hydrogen atom except a) when $R^2$ and $R^3$ both represent hydroxymethyl group, or b) when $R^2$ and $R^3$ together form the methylidene group (=$CH_2$), or c) when $R^1$ represents N-(2'-hydroxyethyl)aminomethyl, N-(2'-aminoethyl) aminomethyl, N-(2'-(glucosamine)aminomethyl.
2. The compound according to claim 1, wherein $R^1$ represents hydrogen atom, and $R^2$ and $R^3$ are selected from the group consisting of: hydrogen atom, hydroxymethyl and (N-pyrrolidinyl)methyl with the proviso that only one of $R^2$ and $R^3$ represents hydrogen atom.

TABLE 1

Cytotoxicity of the compounds on cell lines

| Origin | Cell | $IC_{50}$ μmole/L, after 72 hrs incubation time | | | | | | | | | |
|---|---|---|---|---|---|---|---|---|---|---|---|
| Compound | lines | SN38 | 1 | 2 | 3 | 4 | 5 | 6 | 7 | CC1 | CC2 |
| Breast | MCF7 | 0.66 | 0.81 | 0.96 | 15.93 | 14.91 | | 11.12 | 6.7 | 0.99 | 1.43 |
| Colon | HT29 | 0.02 | 0.60 | 0.49 | 9.481 | 14.77 | 0.15 | 6.98 | 2.50 | 0.07 | 0.24 |
| Blood | HL60 | 0.002 | 0.011 | 0.007 | 0.72 | 1.89 | | 0.33 | 0.11 | 0.012 | 0.014 |
| Lung | A549 | 0.028 | 0.204 | 0.272 | 4.27 | 6.54 | 1.94 | 5.22 | 1.17 | 0.071 | 0.083 |
| Normal cells | CRL1790 | 4.98 | 24.44 | 21.83 | 382.00 | 62.00 | 92.23 | nontoxic >1000 | nontoxic >1000 | 80.52 | 237.00 |

3. The compound according to claim 1, wherein $R^1$ represents (N-azetidinyl)methyl, and $R^2$ and $R^3$ are selected from the group consisting of: hydrogen atom and hydroxymethyl with the proviso that only one of $R^2$ and $R^3$ represents hydrogen atom.

4. The compound according to claim 1, selected from a group consisting of:
- 5-(R)—(N-pyrrolidinyl)methyl-7-ethyl-10-hydroxycamptothecin,
- 5-(S)—(N-pyrrolidinyl)methyl-7-ethyl-10-hydroxycamptothecin,
- 5-(R)-hydroxymethyl-7-ethyl-10-hydroxycamptothecin,
- 5-(S)-hydroxymethyl-7-ethyl-10-hydroxycamptothecin,
- 5-(S)—(N-azetidinyl)methyl-7-ethyl-9-hydroxymethyl-10-hydroxycamptothecin,
- 5-(R)—(N-azetidinyl)methyl-7-ethyl-9-hydroxymethyl-10-hydroxycamptothecin,
- 5-(S)—(N-azetidinyl)methyl-7-ethyl-9-(N-azetidinyl)methyl-10-hydroxycamptothecin,
- 5-(R)—(N-azetidinyl)methyl-7-ethyl-9-(N-azetidinyl)methyl-10-hydroxycamptothecin,
- 5-(R)-hydroxymethyl-7-ethyl-9-(N-azetidinyl)methyl-10-hydroxycamptothecin,
- 5-(S)-hydroxymethyl-7-ethyl-9-(N-azetidinyl)methyl-10-hydroxycamptothecin,
- 5-(S)-hydroxymethyl-7-ethyl-9-hydroxymethyl-10-hydroxycamptothecin,
- 5-(R)-hydroxymethyl-7-ethyl-9-hydroxymethyl-10-hydroxycamptothecin,
- 5-methylidene-7-ethyl-10-hydroxycamptothecin and
- 5,5-bis(hydroxymethyl)-7-ethyl-10-hydroxycamptothecin.

5. The compound according to claim 1, selected from a group consisting of:
- 5-(R)-hydroxymethyl-7-ethyl-9-(N-azetidinyl)methyl-10-hydroxycamptothecin and
- 5-(S)-hydroxymethyl-7-ethyl-9-(N-azetidinyl)methyl-10-hydroxycamptothecin.

* * * * *